United States Patent
Jones et al.

(10) Patent No.: US 8,977,016 B2
(45) Date of Patent: Mar. 10, 2015

(54) METHOD AND SYSTEM FOR CHECKING THE DIAGNOSTIC QUALITY OF A MEDICAL SYSTEM

(75) Inventors: Cheryl Ruth Jones, Hubertus, WI (US); Tabb Alan Patz, New Berlin, WI (US); Chetan H. D., Bangalore (IN); Arun Kumar Chandrashekarappa, Bangalore (IN); Navin Kumar Sharma, Bangalore (IN)

(73) Assignee: General Electric Company, Schenectady, NY (US)

( * ) Notice: Subject to any disclaimer, the term of this patent is extended or adjusted under 35 U.S.C. 154(b) by 1067 days.

(21) Appl. No.: 12/615,976

(22) Filed: Nov. 10, 2009

(65) Prior Publication Data

US 2011/0110565 A1     May 12, 2011

(51) Int. Cl.
    *G06T 7/00*                (2006.01)
    *G06F 19/00*             (2011.01)

(52) U.S. Cl.
    CPC .................................. *G06F 19/3412* (2013.01)
    USPC ....................................................... 382/128

(58) Field of Classification Search
    CPC ... H04L 41/22; G06F 3/0484; G06F 19/3406; A61B 6/46
    USPC ............................................ 715/736; 382/128
    See application file for complete search history.

(56) References Cited

U.S. PATENT DOCUMENTS

| | | | |
|---|---|---|---|
| 6,050,731 A * | 4/2000 | Matsui | 400/74 |
| 6,665,425 B1 | 12/2003 | Sampath et al. | |
| 7,483,939 B2 | 1/2009 | Mussack et al. | |
| 7,496,222 B2 | 2/2009 | Mussack et al. | |
| 7,515,682 B2 | 4/2009 | Li et al. | |
| 7,652,716 B2 * | 1/2010 | Qiu et al. | 348/370 |
| 2006/0159325 A1 * | 7/2006 | Zeineh et al. | 382/128 |
| 2006/0239589 A1 | 10/2006 | Omernick et al. | |
| 2007/0165141 A1 | 7/2007 | Srinivas et al. | |
| 2008/0144897 A1 | 6/2008 | Lal et al. | |
| 2008/0184126 A1 * | 7/2008 | Habas et al. | 715/736 |
| 2008/0184254 A1 | 7/2008 | Bernard et al. | |
| 2009/0169073 A1 * | 7/2009 | Areste et al. | 382/128 |
| 2010/0238462 A1 * | 9/2010 | Reitz et al. | 358/1.9 |

* cited by examiner

*Primary Examiner* — Michelle L Le (57) ABSTRACT

A system and a method are provided that may be used to determine the suitability of a client for use in medical diagnosis. Multimedia content may be presented on the client and used to elicit responses from a user indicative of the suitability of the client for use in medical diagnosis. The elicited responses may be used to determine the suitability of the client for medical diagnosis.

19 Claims, 5 Drawing Sheets

//patents/US8977016B2/page1

METHOD AND SYSTEM FOR CHECKING THE DIAGNOSTIC QUALITY OF A MEDICAL SYSTEM

BACKGROUND OF THE INVENTION

The subject matter disclosed herein relates to medical systems. More specifically, the subject matter disclosed herein relates to methods and systems that may be employed to check the multimedia quality of a medical diagnostic system.

Medical diagnostic systems may include remote viewing systems whose displays are capable of rendering and manipulating a variety of multimedia for diagnostic display purposes. That is, the remote viewing systems are used to review images, video, waveforms (e.g., ECG, EKG), and audio that may be used for medical diagnosis. Typically, remote viewing systems include custom-built hardware. The custom-built hardware is capable of displaying and manipulating images or other media in sufficient detail that a diagnosis may be determined. However, providing custom-built hardware in order to enable remote diagnostics is very costly. An alternative, more economical approach, would use off-the-shelf hardware. However, off-the-shelf hardware such as monitors and computing devices (e.g., desktop computers, workstations, laptops, tablets, personal digital assistants, cell phones) is not standardized and may or may not have the display properties and the processing power capable of enabling remote diagnosis.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a method for investigating the diagnostic properties of clients includes using a client to present an image indicative of diagnostic image quality. A set of user inputs may then be collected that may be based on the presented image. The collected user inputs may then be used to determine the diagnostic suitability of the client.

In a second embodiment, a method may include using a remote client that may be communicatively connected to a remote medical server to download an image. The image may then be used to determine the suitability of the remote client for use in medical diagnosis.

In a third embodiment, a computer-readable medium including computer code may be adapted to download an image from the server and present the image to the user. The user may then give responses indicative of the image quality. The user responses may be collected and utilized by the computer code to determine the diagnostic capabilities of the client.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In the medical field, many different sources producing different types of multimedia information are available for diagnosing and treating patient conditions. X-ray radiography, computer tomography (CT), magnetic resonance imaging (MRI), ultrasound, electrocardiograms (EKG), electroencephalograms (EEG), positron emission tomography (PET), and so forth, may be used to produce multimedia such as images, video, waveforms, audio, and others that may be used in the diagnostic process. The multimedia may be stored in electronic databases and may be accessed by remote clients. A diagnostician may use the remote clients to display and manipulate (e.g., zoom, rotate, pan, pause) the multimedia as appropriate. Off-the-shelf (OTS) clients may be used to replace custom-built remote clients, however, OTS hardware varies in its performance capabilities, and, therefore, only some OTS hardware components may be useful for diagnostic purposes. More specifically, OTS hardware that is be capable of supporting certain image resolutions, aspect ratios, live pixel counts, pixel pitch, frame rates, volume levels, grayscale differences, fine grayscale detail, varying grayscale, aspect ratios, continuity, monitor types, display response times, contrast ratios, brightness, color depths, color gamut, and/or refresh rates may be useful for diagnosis purposes while other OTS hardware that cannot provide the desired properties may be unsuitable. Accordingly, the disclosed embodiments include systems and methods for detecting and analyzing a plurality of diagnostic properties, including the display properties and multimedia manipulation properties, of OTS clients.

OTS clients may include, for example, computer desktops, computer workstations, computer desktops, laptops, tablets, personal digital assistants (PDAs), cell phones, and so forth. Monitors may include, for example, single or multiple computer monitors, televisions, projectors, cell phone screens, PDA screens, and so forth. In one embodiment, OTS clients may be communicatively connected to a server as described in more detail with respect to FIG. 1 below. Software may be distributed to a remote client and used to run a plurality of component checks and question-answer sessions. The component checks may automatically test the properties of certain components such as the central processing unit (CPU), the graphics card, the graphics driver (e.g., Open GL®, Linux® framebuffer, DirectX®, ATI Radeon®), the hard drive, the monitors, and so forth.

The question-answer sessions may include the presentation of different types of multimedia, including calibration images, followed by questions designed to obtain responses that detail the level of performance of the OTS hardware (e.g., choppiness of video playback, display quality, audio fidelity, and waveform fidelity) in playing or displaying the multimedia. New questions may be derived based on the answers to previous questions. The software may then analyze the results of the various component checks and question-answer sessions by using a knowledge base. The software may then provide a summary of findings, which may include the suitability or unsuitability of the OTS client for use in medical diagnostics. In one embodiment, the analysis of the results may include the creation of performance baselines based on the component checks and/or the question-answer sessions. In this embodiment, the performance baselines may then be compared against minimum performance baselines to determine the suitability or unsuitability of the OTS client for use in medical diagnostics.

Figure 1:
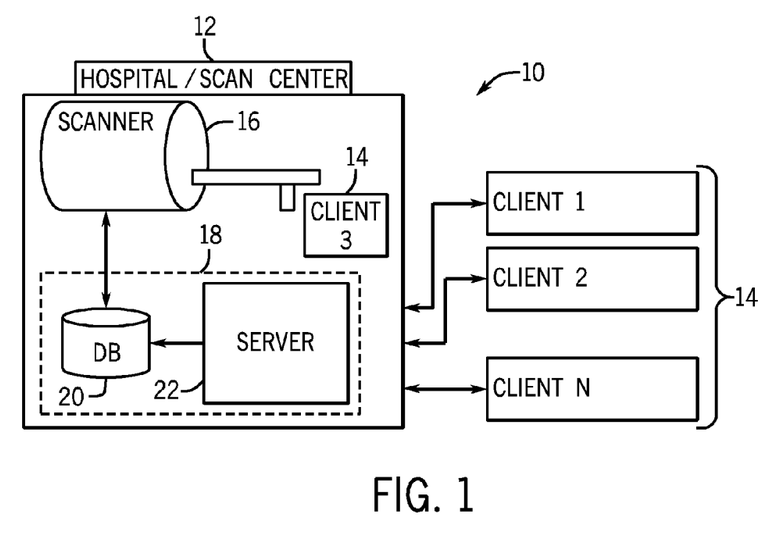
FIG. 1 illustrates an embodiment of a medical information system including a medical scanner, a database, a server, and a plurality of clients.

Turning to FIG. 1, the figure depicts an embodiment of a medical information system 10 including a hospital/scan center 12 and a plurality of clients 14. The clients 14 may include a combination of remote clients, i.e., clients 14 located outside of the hospital/scan center 12, and local clients, i.e., clients 14 located inside of the hospital/scan center 12. The clients 14 may include a variety of OTS hardware and operating systems from an assortment of vendors. For example, a client 14 may include an Apple® laptop running the Snow Leopard® operating system (OS), a Dell® workstation running the Windows Vista® OS, a Toshiba® tablet running the Windows XP Tablet PC Edition® OS, or a Hewlett-Packard® desktop running the Linux® OS. As can be appreciated, clients 14 may include computing platforms from any number of vendors running any number of different OSes.

In certain embodiments, the hospital/scan center 12 may be communicatively connected to the clients 14, such as through a local area network (LAN), a wide area network (WAN), a wireless network, the internet, a dedicated line (e.g., T1, T2, T3), or a modem. Other clients 14 may not be communicatively connected to the hospital/scan center 12 but may have software and medical images distributed to the client 14 through computer storage media, such as a DVDs, CDs, flash drives, USB drives, and so forth.

The hospital scan/center 12 may include a scanner 16, which may be used to scan and store medical multimedia in a data repository 18. In certain embodiments, the scanner 16 may include an MRI, a CT scanner, an X-ray radiography system, a PET scanner, an ultrasound scanner, a tomosynthesis system, and others. Medical multimedia may be generated by the scanner 16 and/or by other devices such as a camera, a video recorder, an audio recorder, and/or a waveform recorder (e.g., electrocardiogram monitor, blood pressure monitor, electroencephalogram monitor), and stored in the data repository 18. The data repository 18 may include a database 20 and a server 22. The database 20 may store a plurality of files having a variety of multimedia file formats including images (e.g., "DICOM", "HL7", "IEEE 1073", "JPEG", "GIF", "PNG", "XCF", "SVG", "PDF"), video ("DICOM", "HL7", "IEEE 1073", "MPEG", "AVI", "MP4", "QUICKTIME"), waveform ("MFER"), audio ("DICOM", "HL7", "IEEE 1073", "MP3", "WAV", "FLAC"), and so forth. It is to be understood that the file formats listed above are only examples of a wide variety of electronic formats that may be used.

The database 20 may be a relational database, a network model database, a hierarchical model database, a flat-file database, or a combination thereof. Indeed, any type of database that is able to store and retrieve electronic data may be used. The server 22 may serve as a front-end to the database 20 and may provide access to the data residing in the database 20. Additionally, the server 22 may also store some of the same data stored in the database 20, for example, for caching purposes. Clients 14 may communicate with the server 22 in order to access the multimedia files, software, patient information, billing records, and so forth. The server 22 may also store, for example, software that may be distributed to the clients 14 and used to analyze the clients 14 for suitability for use in diagnosis as discussed in more detail with respect to FIG. 3 below.

Figure 2:
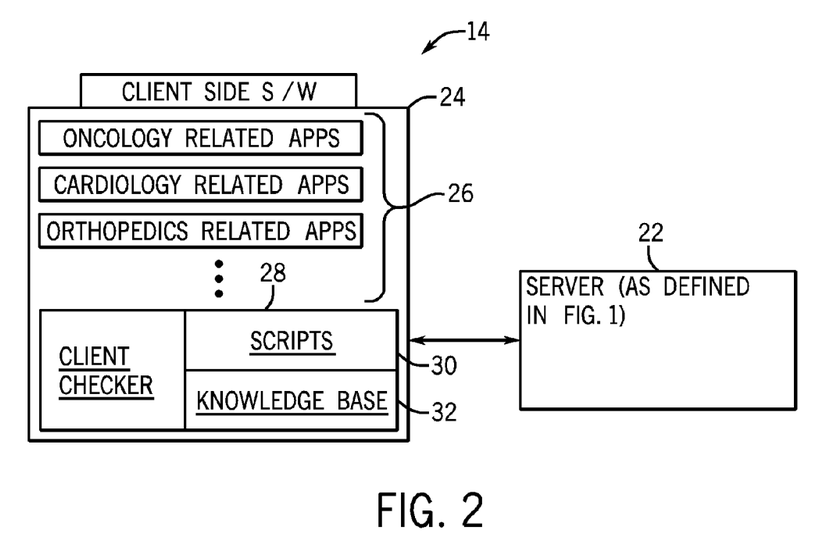
FIG. 2 illustrates an embodiment of a client-side software stack including a client checker application.

FIG. 2 depicts an embodiment of a software stack 24 residing in a client 14. In the depicted embodiment, the software stack 24 may include, for example, medical applications 26 (e.g., oncology applications, cardiology applications, orthopedic applications) that may be installed in the client 14. In one embodiment, the software stack 24 may also include a client checker application 28. As mentioned above with respect to FIG. 1, the client checker application 28 may be distributed to the client 14 through a server 22 communicatively connected to the client 14 or through distributed computer media (e.g., DVDs, CDs, flash drives, usb drives). Different clients 14 may have different operating systems (OSes). Accordingly, in one embodiment, the client checker application 28 may be written in a cross-platform computer language that may be executed in a wide variety of OSes such as Java®, Javascript®, HTML, Python®, Perl®, Ruby, Flash®, Shockwave®, or a combination thereof. Additionally or alternatively, different versions of the client checker application 28 may be written in respective computer languages designed to support a specific OS, for example, in C# supporting the Microsoft Windows® OS, in Objective-C® supporting the Macintosh® OS, and/or in C/C++ supporting the Linux® OS. Further, in embodiments where the client 14 is communicatively connected to the server 22, the client checker application 28 may be written in a computer language designed to be executed in the server 22, for example, as Microsoft® Active Server Pages (ASP), JBoss® pages, and others. The flexibility in distribution and cross-platform execution allows the client checker application 28 to support a wide variety of computer platforms. Indeed, any type of computing device capable of driving any type of display may be supported.

The client checker application 28 may include a set of scripts 30 and a knowledge base 32. In certain embodiments, the scripts 30 may include component check scripts that may be used, for example, to detect and analyze the underlying hardware of the client 14. The scripts 30 may also include computer instructions to execute a series of question-answer sessions which may result in the creation of a performance baseline as described in more detail with respect to FIG. 3 below. The knowledge base 32 may, for example, include data describing a minimum recommended performance baseline and data related to the component checks (e.g., list of component types, list of manufacturers, list of performance measures). The knowledge base 32 may also include the questions-answer sessions and the decision criteria that may be used to compare a performance baseline of the client 14 against a minimum recommended baseline.

Figure 3:
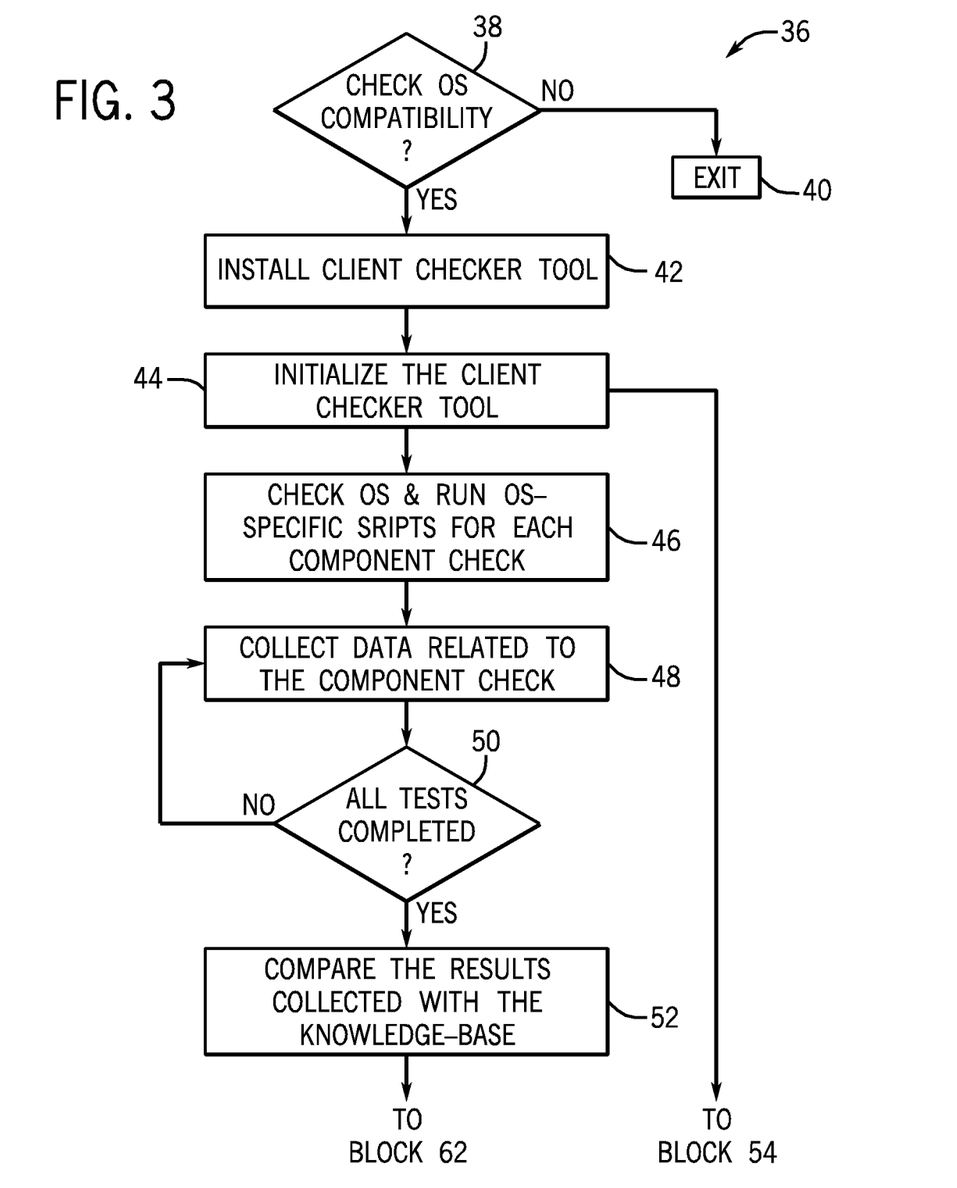
FIG. 3 illustrates a flowchart depicting an embodiment of a method that may be used to detect if a remote client may useful in medical diagnostics.

Turning to FIG. 3, a flowchart depicts an embodiment of a workflow logic 36 that may be used, for example, by the client checker application 28 (shown in FIG. 2), to give an indication of the suitability of the client 14 for use in medical diagnosis. The logic 36 may first determine (decision 38) if the OS of the current client 14 is compatible with the latest embodiments of the client checker application 28. In one embodiment, the check for OS compatibility may be automated. That is, an installer program may use application programming interface (API) calls to check for OS compatibility. The installation program may then determine from the result of the API calls if the OS is compatible. In another embodiment, the user may be asked to select from a list of OSes and the selection may be used to determine if the OS is compatible.

If the OS is determined to be incompatible with embodiments of the client checker application 28 then the workflow logic 36 may end (block 40). If the OS is determined to be compatible with embodiments of the client checker tool 28 then workflow logic 36 may install (block 42) the client checker application 28 onto a client 14. In one embodiment, the installation of the client checker application 28 may include connecting to the server 22 (shown in FIG. 1) and downloading a set of scripts 30 and a knowledge base 32. In another embodiment, the installation of the client checker application 28 may be performed by executing an installation program which may access the scripts 30 and the knowledge base 32 from a storage medium such as a DVD, CD, flash card, or floppy drive. It is to be understood that as in most software installation processes, other actions may take place such as copying files to a hard drive, updating a system registry, creating links to software libraries, and so forth.

The workflow logic 36 may then initialize the client checker application 28 (block 44) by, for example, executing the client checker application 28 in the client 14's processor. In certain embodiments where the client 14 is communicatively connected to the server 22, the initializing may include connecting to the server 22, for example, to establish that the connection is working, to exchange files (e.g., to upgrade to a newer version of the client checker software 28), and so forth. In one embodiment, after the initialization process is completed, the workflow logic 36 then may split into two logic branches which may be executed concurrently or sequentially.

A first logic branch (i.e., left branch after block 44) may be capable of executing automated component checks and a second logic branch (i.e., right branch after block 44 depicted in FIG. 4) may be capable of executing question-answer sessions. At the first logic branch, an OS check may be performed (block 46) that may be able to determine the specific type and software version of the OS (e.g., Windows® 7, Windows Vista® Service Pack 2, Apple® Snow Leopard®, Linux® Ubuntu® 9.04) being used by the client 14. The workflow logic 36 may then execute OS-specific scripts, each script capable of performing a check on one or more hardware or software components of the client 14. Some example components that may be tested include the CPU, the random access memory (RAM), the basic input output system (BIOS), the hard drive, the graphics card (e.g., external graphics card, on-chip graphics card), the graphic drivers (e.g., Open GL®, Linux® framebuffer, DirectX®, ATI Radeon®), the audio drivers (e.g., Windows® Soundblaster® driver, Linux® ALSA driver, Apple® M-Audio® driver), and so forth. A component check may consist of, for example, a set of tests or API queries designed to obtain the manufacturer, model name, and version, of the component.

The workflow logic 36 may then collect data (block 48) related to the component check. It is to be understood that different types of data may be collected depending on the type of component that is being checked. For example, if the component is the CPU, the data collected may include the number of cores present, the manufacturer (e.g., Intel®, AMD®), the clock speed, the types and sizes of the on-chip buffers, and so forth. In another example, if the component is the graphics card component, the data may include the manufacturer and the model of the graphics card (e.g., ATI Radeon®, Nvidia® GeForce®), the manufacturer and the type of graphics driver, and so forth. Similarly, if the component is the audio component, the data may include the manufacturer and the type of audio driver used, and so forth.

In certain embodiments, the component check may also include a check of the current OS display settings being used by a monitor to display the medical information. The component check of the display settings may be used to determine the screen refresh rate, dots per inch (DPI), color quality (e.g., 16 bit, 32 bit), and so forth. It is to be understood that in some embodiments, multiple monitors may be used by the same client 14. In such embodiments, the display settings component check may check the display settings for each one of the multiple monitors. The logic 36 then determines (decision 50) if all of the component check tests have being completed. If there are still components that have not undergone a component check then the logic 36 repeats the collection of data related to the component check (block 48) until all components have been checked.

Once all the component checks have been completed, logic 36 may then compare (block 52) the results of the component check to data present in the knowledge base 32. The comparison may involve determining if any components failed to meet certain baseline specifications. For example, the CPU component of client 14 may run at a clock speed of 500 MHz yet the baseline specification may call for a CPU running at a clock speed of at least 1 GHz. Similarly, the current graphics driver may have a version 9.0a of DirectX® yet the baseline specification may call for using DirectX® 10.0 or better. Other example baseline specifications may include minimum baselines for the hard drive, BIOS, audio driver, monitor, and so forth.

Figure 4:
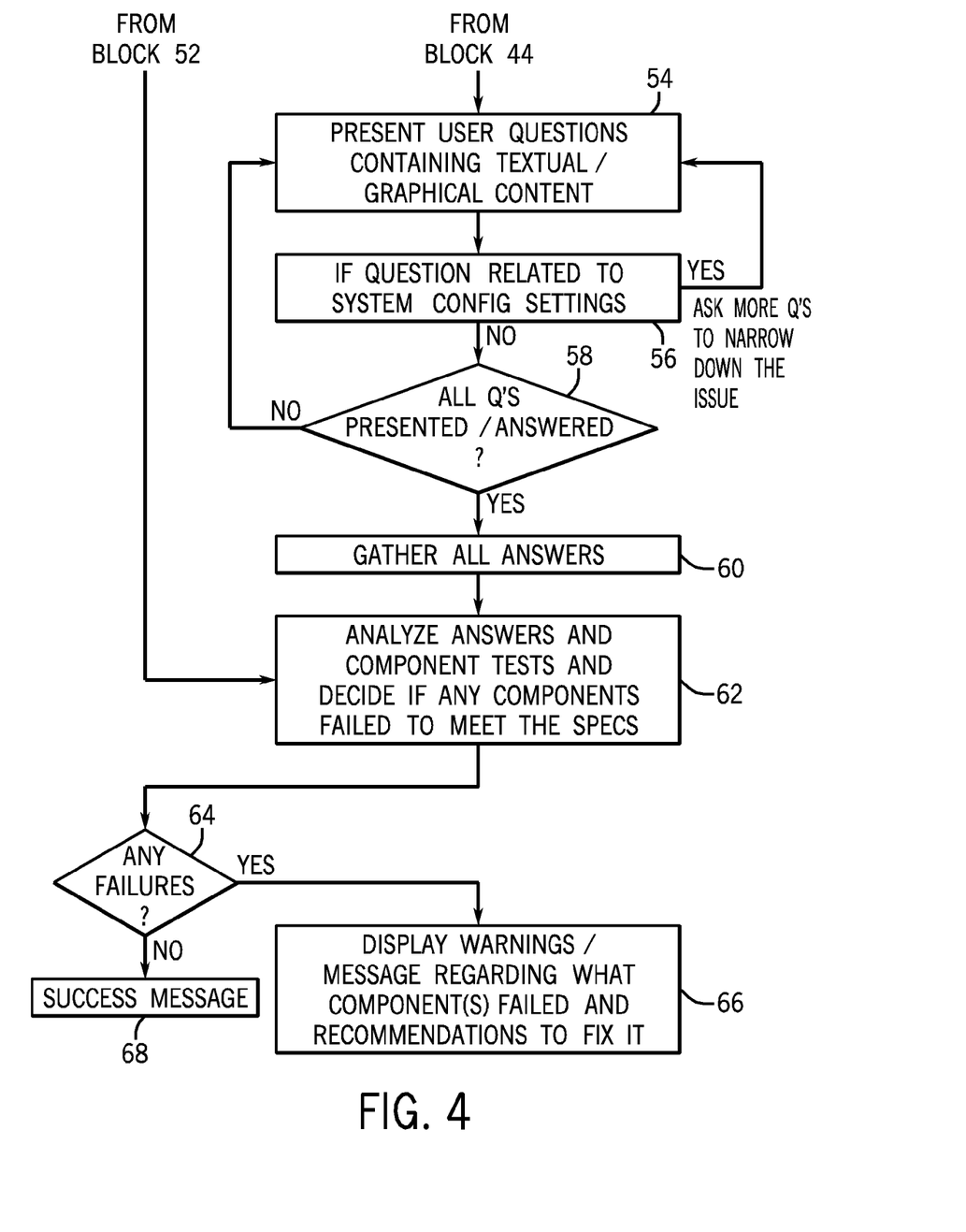
FIG. 4 illustrates a continuation of the flowchart of FIG. 3 depicting an embodiment of a method that may be used to detect if a remote client may useful in medical diagnostics.

Returning to the second logic branch (i.e., right branch after block 44) depicted in FIG. 4, the second logic branch may present to the user a series of questions that may contain textual, graphical, video, and/or audio content, or a combination thereof (block 54). The questions may include presenting multimedia content for the user to evaluate. Questions may then be asked relating to how well the user perceives the performance (e.g., display quality, video performance, audio quality) of the client 14 hardware when observing and/or listening to the multimedia content. In certain embodiments, the multimedia content being presented may include a set of grayscale images (i.e., images composed of shades of gray) such as the image described in more detail with respect to FIG. 5 below.

In other embodiments, the set of questions may include questions related to the video performance capabilities of the client 14. A video may be displayed and questions may be asked regarding, for example, the level of choppiness (i.e., lost frames) of the video, the ability of the video to stay in synch with an audio track, the ability of the video to be viewed at full screen, and so forth. Another set of questions may include questions related to the graphics rendering capabilities of the client 14. A 3-dimensional (3D) object may be rendered on the client's 14 display and the questions may relate to the time it takes to render the object, the time it takes to resize the object, the time it takes to rotate the object, and so forth. Yet another set of questions may include questions related to the audio performance of the client 14. The questions may include questions on the capability to hear sounds at a certain volume level, the capability to hear certain sounds (e.g., tones, frequencies, left speaker only sounds, right speaker only sounds), the ability to hear sounds without skipping or distortions (i.e., alterations of the original recording), and so forth.

Returning to block 56 of the workflow logic 36, if the question being asked (decision 58) relates to system configuration settings (e.g., display settings, sound system settings, graphics acceleration settings) then more questions may be asked (block 54) in order to narrow down the issue of interest. For example, the user may be presented with an image consisting of grayscale differences and asked to answer (e.g., yes, no) if the user can detect the differences in gray. If the user can see the grayscale differences then the user may be presented a different image or directed to a different portion of the same image and asked a set of questions related to fine grayscale detail as described in more detail in FIG. 5 below. The logic 36 may iterate through decision 56 and block 54, asking a plurality of questions so as to narrow down the issue of interest.

If all of the questions have not been presented (decision 58), then the logic 36 may continue asking questions (block 54) until all the questions are presented. The logic 36 may gather the answers to each question (block 60). In certain embodiments, some of the answers to the questions may include instructions that help the user, for example, in reconfiguring certain properties of the client's 14 components. For example, if the user answers that the display does not seem to show grayscale variations then the logic 36 may instruct the user to adjust the client 14 monitor's contrast and/or brightness in order to properly view the grayscale variations. Instructions may also be given by the logic 36 as part of the preparation for the next round of questions, for example, by instructing the viewer to set the client 14 volume controls to a certain level (e.g., 50% volume, 75% volume, 100% volume), to set the monitor at a certain contrast and/or brightness, resolution, bit depth, and so forth.

Once the question-answer session has been finalized, the logic 36 may analyze both the answers and the component checks in order to decide if any components failed to meet the specifications (block 62). As mentioned above, a knowledge base may be used to compare a minimum performance baseline to a performance baseline created by using the answers and the component checks. If it is determined (decision 64) that there are any failures (e.g., a component is below the baseline), then a set of warnings, a set of detailed messages regarding the failed components, and/or a set of recommendations on how to fix any failures may be displayed (block 66). The recommendations may include instructions to the user, for example, to upgrade a software component (e.g., graphics driver, graphics library, audio driver, audio library) and/or a hardware component (e.g., monitor, graphics card, CPU, hard drive, CD drive, DVD drive, network card, speakers). If there are no failures then a success message (block 68) may be displayed, including a summary of the component checks and the question-answer sessions.

Figure 5:
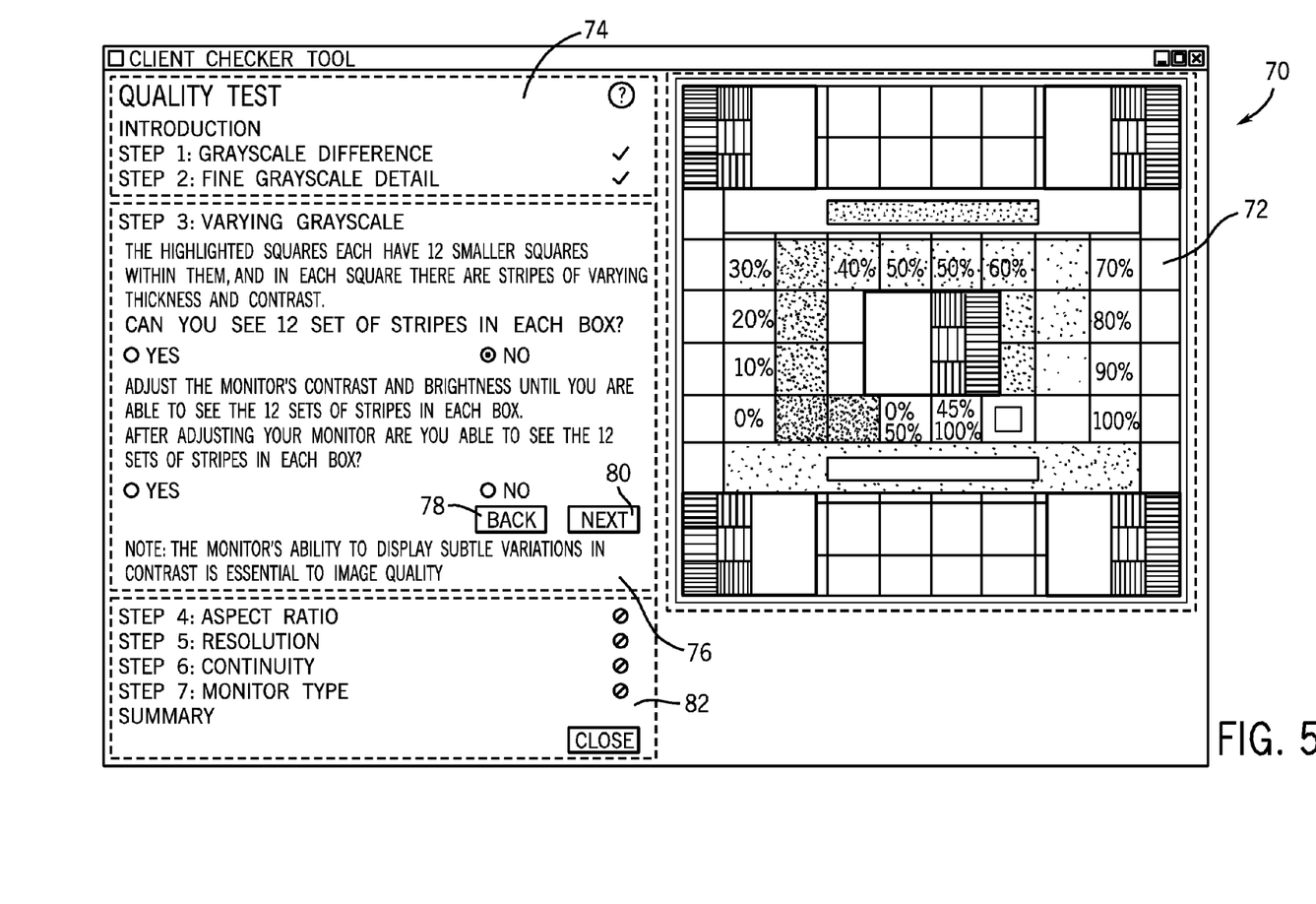
FIG. 5 depicts an embodiment of a screen of a client checker application.

Turning to FIG. 5, the figure depicts an embodiment of an example screen 70 of the client checker application 28 (shown in FIG. 2) that may be used in detecting the suitability of a client 14 for use in medical diagnosis. As mentioned above, the screen 70 may include an area 72 that may be used to display multimedia content. In the area 72 depicted in FIG. 5, a grayscale image is displayed consisting of a plurality of gray, white, and black squares. It is to be understood that other types of multimedia content, for example, color images, video, audio signals, and/or waveforms, may be presented. A set of questions related to the multimedia content being presented may then be displayed.

Some questions related to the grayscale image shown in area 72 of FIG. 5 include questions on grayscale differences (i.e., Step 1), fine grayscale detail (i.e., Step 2), varying grayscale (i.e., Step 3), aspect ratio (i.e., Step 4), and resolution (i.e., Step 5). Other images may be used for questions on continuity (i.e., Step 6) and monitor type (i.e., Step 7). Grayscale difference questions may be designed to elicit responses based on the ability of the monitor to display different levels of gray, for example, by displaying squares ranging from 0% (white) squares to 100% (black) squares. Fine grayscale detail questions may be designed to elicit responses based on the ability of the monitor to display finer gray colors, for example, by displaying a first box having a smaller second box inside the first box where the second box has a slightly different gray color. Varying grayscale questions may be designed to elicit responses based on the ability of the monitor to display striped squares where each striped square has stripes of different thicknesses, contrasts, and/or gray variations.

Aspect ratio questions may be designed to elicit responses based on the ability of the monitor to display boxes of the same or different width and height. Resolution questions may be designed to elicit responses based on the ability of the monitor to display striped boxes having alternating stripe pairs of white and black stripes where the stripes have even thicknesses and where the box does not show any gray colors. Continuity questions may be designed to elicit responses based on the ability of the monitor to display a gray image having a spectrum of gray without also showing banding (e.g., concentric rings), or bleeding (i.e., unwanted grayness or color). Monitor type (i.e., monitor issues) questions may be designed to elicit responses based on type of monitor being used (e.g., liquid crystal display, cathode ray tube) and the ability of the monitor to display white or colored dots against, for example, a black background image. It is to be understood that a variety of multimedia that may provide an indication of the quality of the display may be presented. For example, color images may be displayed in addition to or instead of grayscale images. Questions may then be presented based on the quality of the color, such as color depth, continuity, resolution, aspect ratio, and so forth. Indeed, any type of multimedia that may allow for testing the capabilities of the hardware and software to properly present the multimedia may be used.

Continuing with FIG. 5, the screen 70 may include an area 74 that may be used to display the current status of the client checker software 28. For example, the area 74 displayed in FIG. 5 shows that the client checker program's current status is that of executing a quality test and having completed two steps, i.e., "Step 1—Grayscale Difference" and "Step 2—Fine Grayscale Detail." A status indicator icon, such as a checkmark or a stop sign, may be displayed to the right of the textual label of the steps and used to denote that the steps that have been completed successfully (e.g., a checkmark is shown) or unsuccessfully (e.g., a stop sign is shown).

An area 76 of the screen 70 may be used to present the user with certain questions related to multimedia shown in area 74 as described above. A plurality of user controls, for example, text boxes, radio buttons, list boxes, command buttons, dropdowns, and so forth may be provided as part of the area 76 in order to allow the user to enter any number of responses to the questions presented. The area 76 may also display multimedia, for example, when asking questions comparing the multimedia displayed in area 76 with the multimedia displayed in area 74. The area 76 may also include a set of command buttons 78, 80 which may be used to navigate through the question-answer session. A "Back" command button 78, for example, may allow the user to go navigate backwards one question. A "Next" command button 80, for example, may allow the user to navigate forward to the next question. In one embodiment, the "Next" command button 80 may not be enabled (i.e., grayed out and deactivated) until the user answers the current question.

An area 82 of the screen 70 may include a display of the set of questions that have not yet been completed. In the example area 82 of screen 70 depicted in FIG. 5, the area 82 shows that steps 4-7 and a final summary step have not yet been completed. A status icon (e.g., stop sign) may be used to visually denote the lack of completion of these steps. After the completion of all the steps, a summary may be provided such as the example summary described in more detail with respect to FIG. 6 below.

Figure 6:
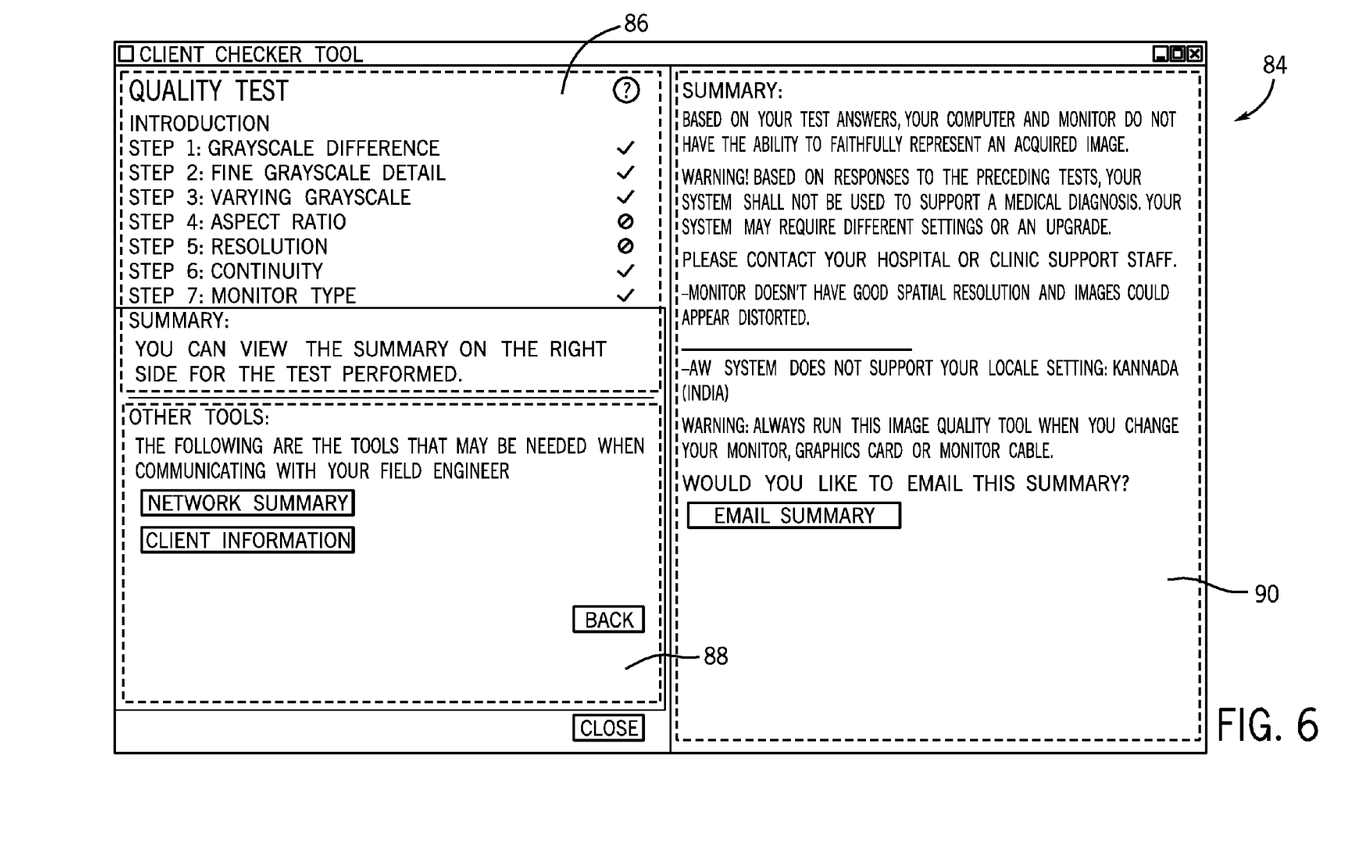
FIG. 6 depicts another embodiment of a screen of the client checker application.

FIG. 6 depicts an example screen 84 that may provide a summary of the results of the various component checks, question-answer sessions, and an indication of the medical diagnosis capabilities of the client 14. The screen 84 may, for example, include an area 86, an area 88, and an area 90. The area 86 may be used to display the current status of the client checker application 28 (shown in FIG. 2). For example, the area 86 depicted in FIG. 6 shows that the client checker application tool has completed seven steps. A status indicator icon such as a checkmark or a stop sign may be displayed to the right of the textual description of the steps and used to denote which steps that have been completed successfully (e.g., a checkmark is shown) or unsuccessfully (e.g., a stop sign is shown). In the example area 86 depicted in FIG. 6, steps 1, 2, 3, 6, and 7 are shown as having been successfully completed while steps 4 and 5 are shown as having been unsuccessfully completed.

An area 88 of the screen 84 may include a series of command buttons that may be used, for example, to execute other functionality. For example, a "Network Summary" command button may execute software instructions that may result in the creation of a summary of the networking capabilities (e.g., network bandwidth, server latency) and networking topology (e.g., internet protocol address, gateway address, domain name server address, subnet mask) of the client 14. A "Client Information" command button may, for example, execute software instructions that may result in the creation of a summary of the client's hardware and software capabilities such as OS used, hard drive usage, software drivers installed, and so forth. The "Client Information" command button may also collect, present, and/or transmit (e.g., email) the data retrieved by the client component checker application 28 (shown in FIG. 2) and the responses to the question-answer sessions as mentioned above.

An area 90 of the screen 84 may include a summary indicative of the capabilities of the client 14 to operate as a medical diagnosis client. The summary may include, for example, a list of issues that would prevent the client 14 from being used as a medical diagnosis client, a list of possible remedial actions that may be taken to upgrade the client 14, and a summary of the ability of the client 14 to function as a medical diagnostic client. The area 90 may also include other user controls, for example, an "Email" command button, that may be used to email and/or save a report of the current analysis to another entity, such as a vendor, for review.

Technical effects of the invention include the capability to discern if an OTS client may be capable of being utilized in medical diagnosis, the capability to automatically check hardware and/or software components of an OTS client against a baseline, and the capability to interact with a user in order to elicit information indicative of the current diagnostic suitability of the OTS client. A computer network may be used to deliver computer code capable of testing the diagnostic suitability of an OTS client. The computer network may also be used to transmit the results of the diagnostic suitability analysis to vendors and to other entities. A wide variety of previously unused OTS hardware may be tested and used to replace expensive custom-built hardware.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for investigating diagnostic properties of a system:
   using a processor on the system to perform the steps of:
   presenting, on a display screen, a test image indicative of diagnostic image quality;
   collecting, on a device communicatively coupled to the display screen, user input based on the presented image;
   analyzing the collected user input based on a specification to establish a performance baseline for the system;
   if the performance baseline does not meet a minimum performance baseline for displaying medical images, displaying a failure indication that the system or a hardware component of the system is unsuitable for displaying diagnostic medical images;
   if the performance baseline does meet the minimum performance baseline, displaying a success indication that the system or a hardware component of the system is suitable for displaying diagnostic medical images.

2. The method of claim 1, wherein the test image indicative of diagnostic image quality comprises a grayscale image.

3. The method of claim 2, wherein the grayscale image comprises an image capable of displaying grayscale differences, fine grayscale detail, varying grayscale, aspect ratio, resolution, continuity, monitor issues, or a combination thereof.

4. The method of claim 1, wherein the test image indicative of diagnostic image quality comprises a color image.

5. The method of claim 1, comprising presenting at least one of a video or a waveform indicative of diagnostic video quality or of diagnostic waveform quality, and collecting user input based on the presented video or waveform.

6. The method of claim 1, comprising presenting an audio signal indicative of diagnostic audio quality, and collecting user input based on the presented audio signal.

7. The method of claim 1, comprising configuring the system to automatically check at least one of the hardware component or a software component in order to determine the suitability of the system for use in medical diagnosis.

8. The method of claim 1, wherein the determining the diagnostic suitability of the hardware component based on the collected user input comprises at least one of communicatively connecting to a medical server to download software or installing software from a computer readable medium, and utilizing the software to collect the user input and to analyze the user input.

9. A method comprising:
using a processor on a client to perform the steps of:
communicatively connecting to a medical server;
downloading a test image from the medical server; and
utilizing the test image to determine the suitability of a hardware component of the client for use in medical diagnosis based on a performance baseline for viewing diagnostic medical images derived for a hardware component of interest, wherein utilizing the test image to determine the suitability of the hardware component of the client for use in medical diagnosis comprises: executing a set of computer instructions to present the test image indicative of diagnostic image quality on a screen display; collecting, on a device communicatively coupled to the client, user input based on the presented test image; using the collected input to determine the performance baseline for the hardware component; displaying a failure indication that the hardware component of the system is unsuitable for displaying diagnostic medical images if the performance baseline does not meet a minimum performance baseline for displaying medical images; and displaying a success indication that the hardware component of the system is suitable for displaying diagnostic medical images if the performance baseline meets the minimum performance baseline for displaying diagnostic medical images.

10. The method of claim 9, wherein the utilizing the test image to determine the suitability of the hardware component of the client for use in medical diagnosis comprises executing a set of instructions to automatically check the hardware component or software components of the client.

11. The method of claim 9, wherein the downloaded test image comprises a grayscale image.

12. The method of claim 11, wherein the grayscale image comprises an image capable of displaying grayscale differences, fine grayscale detail, varying grayscale, aspect ratio, resolution, continuity, monitor issues, or a combination thereof.

13. The method of claim 9, wherein the utilizing the test image to determine the suitability of the hardware component of the client for use in medical diagnosis comprises executing a set of computer instructions to present a video indicative of diagnostic video quality, to collect user input based on the presented video, and to use the collected input to determine the diagnostic suitability of the client.

14. The method of claim 9, wherein utilizing the test image to determine the suitability of the hardware component of the client for use in medical diagnosis comprises executing a set of computer instructions to present at least one of an audio signal indicative of diagnostic audio quality or a waveform indicative of diagnostic waveform quality, collect user input based on the presented audio signal or waveform, and use the collected input to determine the diagnostic suitability of the client.

15. A non-transitory computer-readable medium, encoding one or more routines which, when executed by a processor, cause the processor to perform acts comprising:
presenting a test image on a screen display of a client communicatively coupled to a medical server;
collecting, on a device communicatively coupled to the screen display, user responses indicative of the quality of the test image presented on the client;
analyzing the collected user responses based on a specification to establish a performance baseline for the client; and
if the performance baseline does not meet a minimum performance baseline for displaying medical images, displaying a failure indication that the client or a hardware component of the system is unsuitable for displaying diagnostic medical images;
if the performance baseline does meet the minimum performance baseline, displaying a success indication that the client or a hardware component of the system is suitable for displaying diagnostic medical images.

16. The non-transitory computer-readable medium of claim 15, wherein the test image comprises a grayscale image capable of displaying grayscale differences, fine grayscale detail, varying grayscale, aspect ratio, resolution, continuity, monitor issues, or a combination thereof.

17. The non-transitory computer-readable medium of claim 15, comprising one or more routines which, when executed, cause additional acts to be performed comprising: automatically executing a component check of at least one of the hardware component or a software component, wherein the component check results are used to determine the diagnostic capabilities of the client.

18. The tangible computer-readable medium of claim 15, comprising one or more routines which, when executed, cause additional acts to be performed comprising:
downloading at least one of a video indicative of diagnostic video quality, an audio signal indicative of diagnostic video quality, or waveform indicative of diagnostic waveform quality from the medical server;
presenting the video, the audio signal, or the waveform to a user;
collecting responses from the user indicative of the video quality, the audio signal quality, or the waveform quality; and
determining the diagnostic capabilities of the hardware component or a software component of the client based on the responses from the user.

19. The method of claim 1, wherein the system, when functioning properly, is determined to be suitable or unsuitable for displaying diagnostic medical images.

\* \* \* \* \*